United States Patent [19]

Stanonis et al.

[11] 4,186,608
[45] Feb. 5, 1980

[54] METHOD AND APPARATUS FOR VERIFYING DECLARED CONTENTS OF CONTENTS OF CERTAIN SOLIDS

[75] Inventors: David J. Stanonis; Walter D. King, both of New Orleans; Emory E. Coll, Metairie, all of La.

[73] Assignee: The United States of America as represented by the Secretary of Agriculture, Washington, D.C.

[21] Appl. No.: 925,136

[22] Filed: Jul. 17, 1978

[51] Int. Cl.² ............................................. G01N 9/10
[52] U.S. Cl. ...................................... 73/437; 73/450; 73/451
[58] Field of Search ............... 73/32 R, 437, 433–436, 73/450, 451–454

[56] References Cited

U.S. PATENT DOCUMENTS

| | | | |
|---|---|---|---|
| 2,635,461 | 4/1953 | Groth et al. | 73/434 |
| 2,722,838 | 11/1955 | Roy | 73/451 |
| 2,760,374 | 8/1956 | Gottsch | 73/437 |
| 3,246,504 | 4/1966 | Halff et al. | 73/451 |

FOREIGN PATENT DOCUMENTS 1133474 11/1956 France ..................................... 73/452

OTHER PUBLICATIONS

"A Method for Determining the Moisture Content . . . " by Schmidt, Tappi, vol. 51 No. 4 Apr. 1968 (pp. 164–170).

*Primary Examiner*—Gerald Goldberg
*Assistant Examiner*—Joseph W. Roskos
*Attorney, Agent, or Firm*—M. Howard Silverstein; David G. McConnell; Salvador J. Cangemi

[57] ABSTRACT

An apparatus and method are provided for verification of declared contents in mixed solids, blended textiles, certain pure solids, and other solid substances. The apparatus is assembled from laboratory items and utilizes liquids and instruments. The method requires the measurement of changes in chain length in a chain suspended from the bottom of a float, and appliable values substituted in an equation which utilize densimetric principles to achieve a comparative presentation of values for verification.

4 Claims, 2 Drawing Figures

FIGURE I

METHOD AND APPARATUS FOR VERIFYING DECLARED CONTENTS OF CONTENTS OF CERTAIN SOLIDS

BACKGROUND OF THE INVENTION

1. Field of the Invention

This invention relates to an apparatus and a method for determining densimetric differences in solids. More specifically the invention provides a means of verifying declared proportions or contents of known solids.

2. Description of the Prior Art

In the prior art U.S. Pat. No. 2,664,011 discloses the measurement of densities of liquids, which, of course is unlike the densimetric evaluation of solids.

Kirshenbaum, in his review on density and specific gravity, (Kirshenbaum, I., Density and Specific Gravity. Standen, A. ed. Kirk-Othmer Encyclopedia of Chemical Technology, Volume 6; New York, J. Wiley & Sons, Inc.; 1965: 755-777.) describes the chain-balanced-float recorder as another device for weighing a fixed volume of liquid.

SUMMARY OF INVENTION

This invention consists of an apparatus and a method for verifying declared proportions of the contents of certain solid mixtures. The apparatus comprises a small number of known laboratory pieces, which when assembled to operate in unison serve the useful purpose of providing the operator with a mathematical value useful in determination of density of solids when immersed in certain liquids.

The apparatus consists of a vessel within a vessel, an outer liquid for maintaining a constant temperature, an inner liquid for providing a flotation medium, a float for providing a chamber within which is placed the solid to be evaluated, a variable weight (such as a chain) secured to the bottom of the float for counterbalancing the sample and stabilizing the location of the float, and a sighting device for determining the precise location of the float when loaded and again when unloaded. The outer liquid is maintained at the selected temperature by a circulating pump.

The method comprises placing the solid within the float after the position of the float-at-rest has been determined, allowing for the float to move freely within the innermost vessel which contains a liquid mixture of known density—either upward or downward—and determining a relocation position, thus obtaining a mathematical value which is then fed into a mathematical equation for computation, to obtain the density of the solid in the known liquid.

The main object of the present invention is to provide a method and a means for verifying declared proportions of known solid constituents.

DESCRIPTION OF THE PREFERRED EMBODIMENTS

Figure 1:
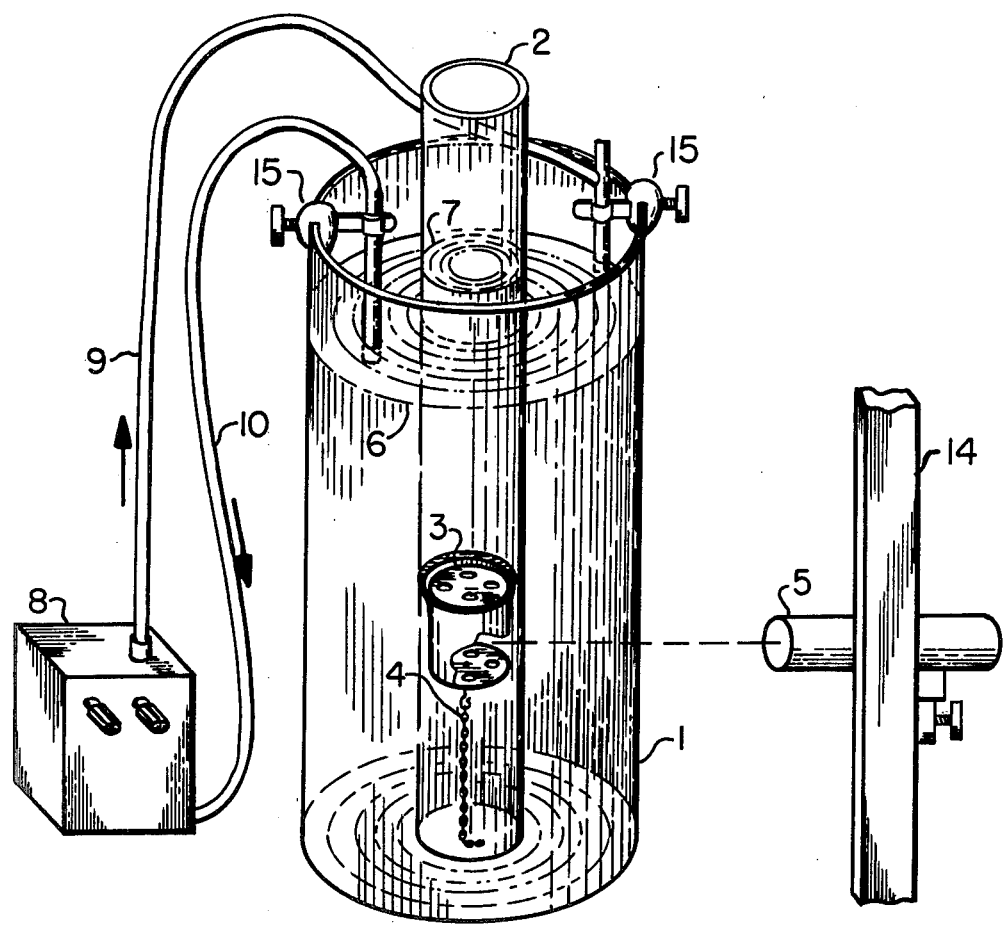
FIG. 1 is a perspective view of the preferred apparatus of this invention.
Figure 2:
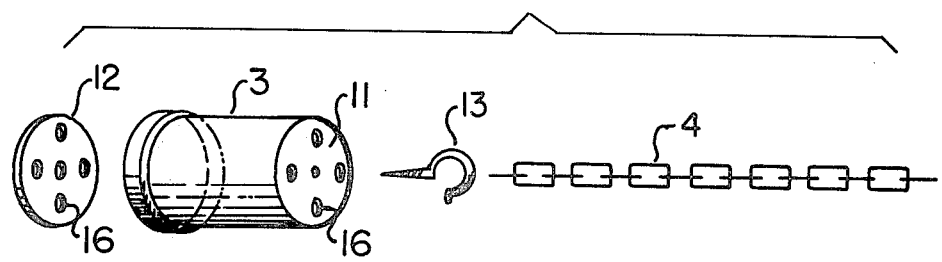
FIG. 2 is an exploded and supplemental view of the float assembly of preferrence to this invention.

The preferred apparatus of this invention, as illustrated in FIGS. 1 and 2, consists essentially of an outer vessel 1, an inner vessel 2, an outer liquid 6, an inner liquid 7, a float 3 (a floating chamber with a perforated top 12 and a perforated bottom 11, a variable weight, preferrably a fine chain 4, which is secured to the float 3 by means 13, tubing 9 and 10 supported by means 15 for maintaining temperatures constant, and auxiliary devices such as a heat regulating pump 8, a sighting device such as a cathetometer 5, and supporting devices 14.

The preferred conditions for a satisfactory operation of the apparatus of this invention require maintaining a constant temperature of the liquid of the inner vessel. That is accomplished by maintaining a constant circulation of water, inward through tubing 9 and outward through tube 10. This maintains the temperature of the inner liquid 7 constant. The vessels 1 and 2 should be transparent and without visual distortion for more accurate viewing. Although a pure liquid 7 is preferred for the inner liquid 7, there are a number of useful liquid mixtures which offer a wide range of densities. Organic liquid mixtures can be made from a number of completely miscible substances varying in density from 0.63 (Pentane) to 3.33 (diiodomethane). Aqueous solutions of salts can be made to vary from a density of unity to as high as 4.9 for concentrated thallium formate-thallium malonate mixtures in water. (From "Density Gradient Techniques", G. Oster and M. Yamamoto, Chemical Reviews, 63, 257 (1963).) The preferred liquid 6 of the outer chamber is water.

In the experimentation which led to the invention the float 3 was made from a polyethylene bottle with modifications for attaching a hook at the bottom so the chain could be attached thereto, and also perforations 16 were instituted for better circulation of the liquid 7; however these preferences were merely because the material was available. In practice it is preferred simply to have liquid 7 to be inert and the float 3 to be inert therein.

The variable weight, fine chain 4, is preferred of low linear density, preferably of about 0.06 g/cm in air weight. The preferred sighting device 5 is a cathetometer.

The preferred method of this invention requires the placement of the unknown or questioned solid or a sample thereof within the float 3 (a floatation chamber which must not permit the escape of the solid during operation of the apparatus, while permitting the flow of liquid 7 through the perforations 16), but this only after a reading of the empty float location has been made and recorded. In practice the preferred reading is made at the very top of the chain. The second and final reading is made when the loaded float has moved and come to its new location (upward or downward). The measurement is the distance of vertical chain from top to bottom. This measurement is carried out twice, the difference recorded, and a computation made to determine the weight of solid in the liquid. The computation requires substitution in the equation . . .

$$\left[\begin{array}{l}\text{Weight of the material} \\ \text{in liquid}\end{array}\right] = -\left(\begin{array}{l}\text{change in} \\ \text{chain length}\end{array}\right) \times \left(\begin{array}{l}\text{linear density} \\ \text{of chain lin} \\ \text{liquid}\end{array}\right)$$

OR $$W_1 = -\Delta \times Z_1$$

and finally substituting the value of $W_1$ obtained from this computation in the following equation:

$$\begin{bmatrix} \text{Density of the} \\ \text{solid material} \\ \text{(questioned)} \end{bmatrix} = \frac{\begin{bmatrix} \text{Weight of} \\ \text{the material} \\ \text{in air} \end{bmatrix} \times \begin{bmatrix} \text{Density of} \\ \text{liquid} \end{bmatrix}}{\begin{bmatrix} \text{Weight of} \\ \text{the material} \\ \text{in air} \end{bmatrix} - \begin{bmatrix} \text{Weight of} \\ \text{the material} \\ \text{in liquid} \end{bmatrix}}$$

Briefly presented as......

$$D_s = \frac{W_a \times D_l}{W_a - W_l}$$

Note:
This is referred to as the verification formula.

In the preferred method of utilizing the invention the steps of the method of this invention are applied to known substances, then the entire procedure is repeated with the unknown, for rapid verification of declared contents of known constituents. The computation of the knowns are applied to the unknowns and the declared contents of the unknowns should be exactly the same as those of the knowns. The method can be applied in the case of differentiating from one blend of textiles to another, from a 22K gold medallion to a 10K gold medallion, and many other solid substances and mixtures thereof.

The following examples are provided to illustrate the invention and should not be construed as limiting the invention in any manner whatever.

EXAMPLE 1

A 2000 ml. graduated cylinder was filled with water at 25° C. The density of water at this temperature is 0.997 g/cc. A flotation chamber was constructed by cutting circular holes throughout the entire surface of a 100 cc polyethylene bottle to permit unrestricted flow of the water from all directions. A wire loop was attached to the bottom of the bottle (aluminum wire). A uniform chain of low linear density, measuring 50 cm. in length was secured to the wire loop. The assembled flotation unit was placed into the graduated cylinder and allowed to come to rest before measuring the distance from the first link under the chamber to the last link which was suspended, making sure that any link in the chain which was not suspended would not be included in the measurement.

A sheet of purported polyethylene was utilized as a specimen which would illustrate the case of an ascending chamber. The sheet was trimmed so as to provide a sample weighing 1.000 g. Upon placing the specimen sample in the float (flotation chamber) the float ascended to a new location vertically at a higher level within the inner vessel. Once the float ceased in its rise a measurement was made and recorded. The applicable values are presented below.

(a) linear density of the chain = 0.0538 g/cm
(b) length of chain with chamber empty = 22.310 cm
(c) length of chain with chamber loaded = 23.635 cm
(d) weight of specimen sample = 1.000 g
(e) incremental change in chain length ($\Delta$) = (23.635 cm−22.310 cm) = 1.325 cm
(f) effective weight ($W_1$) of specimen sample in water = $-\Delta \times Z_1$ = $-1.325$ cm × 0.0538 g/cm = $-0.0713$ g Substituting the values of Example 1 in the verification formula of the present invention the values generated are as follows:

$$D_s = \frac{1.000 \text{ g} \times .997 \text{g/cc}}{1.000 \text{ g} - (-0.713)\text{g}} = \frac{.997\text{g}^2/\text{cc}}{1.0713\text{g}}$$

$$D_s = 0.931 \text{g/cc}$$

Conclusion: The material was determined to be a polyethylene since the literature indicates the polyethylene to range from 0.92 to 0.95.

EXAMPLE 2

To illustrate an instance wherein the float of the invention would descend, in contrast to the ascending float of Example 1, the apparatus and method of Example 1 were duplicated but a sheet of purported Teflon was utilized as the sample specimen. The sheet was trimmed so as to provide a specimen weighing 1.000 g. The initial reading was made, a recording made, the chamber loaded, the chamber was observed descending and was allowed to achieve stability. Once all movement ceased a reading was made and recorded. All values pertinent to Example 2 are presented below:

(a) linear density of the chain = 0.0538 g/cm
(b) length of chain with chamber empty = 22.310 cm.
(c) length of chain with chamber loaded = 12.130 cm.
(d) weight of specimen sample = 1.000 g
(e) incremental change in chain length = 12.130 cm−22.310 cm = −10.180 cm
(f) effective weight of specimen sample in water = Substituting values in $-\Delta \times Z_1 = -(-10.18) \times 0.0538$ g/cm = 0.5477 g Substituting the values of Example 2 in the verification formula:

$$D_s = \frac{1.000 \text{ g} \times 0.997\text{g/cc}}{1.000 \text{ g} - 0.5477} = \frac{0.997\text{g}^2/\text{cc}}{0.4523\text{g}}$$

$$D_s = 2.20 \text{g/cc}$$

Conclusion: The material was determined to be a Teflon since the literature indicates the density of Teflon to be about 2.15.

EXAMPLE 3

To illustrate verification of declared contents in blanded textiles a fabric purported to be a blend containing 68% of polyester and 32% of cotton, by weight, on a dry basis, was utilized as a specimen. The fabric was trimmed so as to provide a sample weighing 1.000 in ambient air (0.9828 gram on a dry basis). Upon placing the specimen sample in the float (floating chamber) the float descended to a new location. Once the float ceased in its descent a measurement was made and recorded. The applicable values are presented below:

(a) linear density of the chain in water = 0.01508 g/cm.
(b) length of chain with chamber empty = 25.28 cm.
(c) length of chain with chamber loaded = 5.26 cm.
(d) incremental change in chain length ($\Delta$) = $-20.02$ cm.
(e) effective weight of specimen in water = $-\Delta \times Z_1 - (-20.02) \times 0.01508 = 0.3019$ g Substituting the values in the verification formula;

$$D_s = \frac{0.9828 \times 0.997}{0.9828 - 0.3019} = 1.439 \text{ g/cc}$$

Conclusion: The cotton/polyester blend contains 68% polyester, within the allowable ±3% because the allowable density range for a cotton/polyester blend made from cotton with a measured density of 1.567 g/cc (measured in water) and a polyester with a measured density of 1.387 g/cm measured in water is 1.435 g/cc (71% polyester) to 1.445 g/cc (65% polyester).

We claim:

1. In a density-measuring apparatus of the type which includes a vessel substantially filled with a liquid; a float in said vessel; a variable weight attached to the bottom of said float to hold it submerged in said liquid; and means to measure the vertical repositioning of said float and variable weight, the improvement, a modification comprising:
   (a) said liquid in said vessel being of a predetermined and constant density; and
   (b) means to secure a solid material of unknown density to said float in addition to said variable weight, and to immerse it in said liquid together with said float, said measuring means thus determining the weight of said solid material in said liquid; wherein said float comprises a hollow chamber whose walls are less dense than said liquid, wherein said walls are perforated to allow said liquid to fill said float when submerged in said liquid; and wherein said walls include access opening means to enable said material to be placed within said hollow chamber in an untethered state.

2. The apparatus of claim 1 wherein said liquid is water; wherein said solid material is of a predetermined weight, (in air); and wherein said measuring means is calibrated to directly determine the density of said material.

3. The apparatus of claim 1 further including means to maintain said liquid at a constant predetermined temperature.

4. The apparatus of claim 1 wherein said variable weight is a chain.

* * * * *

UNITED STATES PATENT AND TRADEMARK OFFICE
CERTIFICATE OF CORRECTION

PATENT NO. : 4,186,608
DATED : February 5, 1980
INVENTOR(S) : David J. Stanonis, Walter D. King and Emory E. Coll It is certified that error appears in the above-identified patent and that said Letters Patent is hereby corrected as shown below:

The title in the above captioned patent should read as follows:

[54] METHOD AND APPARATUS FOR VERIFYING DECLARED CONTENTS OR CERTAIN SOLIDS

Signed and Sealed this

Nineteenth Day of August 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,186,608
DATED : February 5, 1980
INVENTOR(S) : David J. Stanonis, Walter D. King and Emory E. Coll It is certified that error appears in the above—identified patent and that said Letters Patent is hereby corrected as shown below:

The title in the above captioned patent should read as follows:

[54] METHOD AND APPARATUS FOR VERIFYING DECLARED CONTENTS OF CERTAIN SOLIDS

Signed and Sealed this

Twenty-third Day of December 1980

[SEAL]

Attest:

Attesting Officer

SIDNEY A. DIAMOND

Commissioner of Patents and Trademarks